United States Patent
Mizukami et al.

(10) Patent No.: US 11,992,820 B2
(45) Date of Patent: May 28, 2024

(54) REACTION DEVICE AND REACTION METHOD USING FINE BUBBLES

(71) Applicants: CATALER CORPORATION, Kakegawa (JP); NATIONAL UNIVERSITY CORPORATION SHIZUOKA UNIVERSITY, Shizuoka (JP)

(72) Inventors: Tomohito Mizukami, Kakegawa (JP); Yusuke Saito, Kakegawa (JP); Nobuyuki Mase, Hamamatsu (JP)

(73) Assignees: CATALER CORPORATION, Kakegawa (JP); NATIONAL UNIVERSITY CORPORATION SHIZUOKA UNIVERSITY, Shizuoka (JP)

( * ) Notice: Subject to any disclaimer, the term of this patent is extended or adjusted under 35 U.S.C. 154(b) by 556 days.

(21) Appl. No.: 17/271,447

(22) PCT Filed: Sep. 9, 2019

(86) PCT No.: PCT/JP2019/035416
§ 371 (c)(1),
(2) Date: Feb. 25, 2021

(87) PCT Pub. No.: WO2020/054679
PCT Pub. Date: Mar. 19, 2020

(65) Prior Publication Data
US 2021/0322947 A1    Oct. 21, 2021

(30) Foreign Application Priority Data
Sep. 11, 2018  (JP) ................................ 2018-169969

(51) Int. Cl.
*B01J 19/24*    (2006.01)
*B01F 23/23*    (2022.01)
(Continued)

(52) U.S. Cl.
CPC ....... *B01J 19/2485* (2013.01); *B01F 23/2375* (2022.01); *B01J 10/002* (2013.01);
(Continued)

(58) Field of Classification Search
CPC .......................... B01J 19/2485; B01F 23/2375
See application file for complete search history.

(56) References Cited

U.S. PATENT DOCUMENTS

| 2011/0165040 A1 | 7/2011 | Huang et al. |
| 2017/0252717 A1 | 9/2017 | Takase et al. |

FOREIGN PATENT DOCUMENTS

| CN | 105840273 A | 8/2016 |
| EP | 1287884 A2 | 3/2003 |

(Continued)

OTHER PUBLICATIONS

Nov. 19, 2019 International Search Report issued in International Patent Application No. PCT/JP2019/035416.
(Continued)

*Primary Examiner* — Robert A Hopkins
(74) *Attorney, Agent, or Firm* — Oliff PLC

(57) ABSTRACT

A reaction device for reacting a liquid-phase reactant and a gas-phase reactant converted into fine bubbles includes: a porous body that includes a plurality of flow paths and in which the flow paths are separated by porous walls, the porous walls include continuous pores, and the porous body includes a reaction catalyst at least on the surface thereof; a solution supply section for supplying a solution containing a gas-phase reactant and a liquid-phase reactant to the continuous pores in the porous body; and a solution discharge section for discharging solution containing a reaction product obtained when the solution flows through the continuous pores of the porous body.

10 Claims, 2 Drawing Sheets

(51) Int. Cl.
  *B01F 23/2375* (2022.01)
  *B01J 10/00* (2006.01)
  *B01J 35/56* (2024.01)
  *B01J 35/64* (2024.01)

(52) U.S. Cl.
  CPC ............ *B01J 35/56* (2024.01); *B01J 35/643* (2024.01); *B01J 2219/00844* (2013.01); *B01J 2219/00891* (2013.01)

(56) References Cited

FOREIGN PATENT DOCUMENTS

| EP | 2484424 A1 | 8/2012 | |
|----|----|----|----|
| JP | 2014-005217 A | 1/2014 | |
| JP | 2017-019743 A | 1/2017 | |
| JP | 2017-217585 A | 12/2017 | |
| KR | 101865240 B1 | 6/2018 | |
| WO | 02/079128 A1 | 10/2002 | |
| WO | WO-2005084805 A1 * | 9/2005 | .......... B01J 19/2485 |
| WO | 2016/031527 A1 | 3/2016 | |

OTHER PUBLICATIONS

Nov. 19, 2019 Written Opinion of the International Searching Authority issued in International Patent Application No. PCT/JP2019/035416.

May 17, 2022 Search Report issued in European Patent Application No. 19860808.5.

Nov. 7, 2023 Office Action issued in European Application No. 19 860 808.5.

* cited by examiner

REACTION DEVICE AND REACTION METHOD USING FINE BUBBLES

FIELD

The present invention relates to a reaction device using fine bubbles and a reaction method using fine bubbles.

BACKGROUND

The phrase "fine bubbles" refers to bubbles having a diameter of 100 μm or less, and the term "ultrafine bubbles" refers to bubbles having a diameter of 1 μm or less, among fine bubbles. Since these have properties different from those of ordinary bubbles, the applications thereof have been studied in various fields in recent years.

Examples of methods for producing fine bubbles or ultrafine bubbles include a swirling liquid flow method, a pressure dissolution/decompression method, and a micropore method.

In the swirling liquid flow method, a liquid is injected into a cylindrical container at a high speed to form a high-speed swirling flow in the interior thereof, and a pressure drop is generated in the center thereof. Fine bubbles are obtained when gas is introduced from small holes in the lower part of the cylindrical container and the gas is discharged from small holes in the upper part thereof.

In the pressure dissolution/decompression method, gas is pressurized and dissolved in a fluid. The fluid is then rapidly discharged into a liquid under reduced pressure or atmospheric pressure, so that the dissolved gas can precipitate as fine bubbles.

In the micropore method, gas is discharged into a liquid from nano-level micropores.

Further, other methods have been studied. For example, in Patent Literature 1, gas is pressurized with a pump to dissolve the gas in a liquid, and the gas-liquid mixture is flowed through a metal filter having a microporous channel, whereby refined bubbles are obtained. The microporous channel has a length of 30 mm to 60 mm and a pore diameter of 300 μm or less.

In recent years, an organic synthesis method in which fine bubbles are used as a gas phase in a system for reaction between a gas phase and a liquid phase has been studied. For example, in Patent Literature 2, fine bubbles of a reaction gas generated in a fine bubble production device are introduced into a liquid phase to cause the reaction gas to react at normal pressure. Conventionally, when the reaction product of a gas phase and the reaction product of a liquid phase are reacted, it is necessary to maintain the reaction system at a high pressure to dissolve the reaction product of the gas phase in the liquid phase, or to increase the frequency of contact between the gas phase and the liquid phase by subjecting them to strong mechanical agitation. The method described in Patent Literature 2 is useful because the gas phase and the liquid phase can be reacted with high efficiency without the need for high pressure or strong mechanical agitation.

Methods for reacting a gas phase and a liquid phase using fine bubbles are also known from Patent Literature 3 and 4.

CITATION LIST

Patent Literature

[PTL 1] Japanese Unexamined Patent Publication (Kokai) No. 2017-217585

[PTL 2] Japanese Unexamined Patent Publication (Kokai) No. 2017-019743

[PTL 3] Japanese Unexamined Patent Publication (Kokai) No. 2014-005217

[PTL 4] WO 2016/031527

SUMMARY

Technical Problem

According to the investigations by the present inventors, it has been found that in the methods described in Patent Literature 2 to 4, the fine bubbles tend to coalesce, whereby the sizes of the bubbles increase. There is room for improvement in this regard.

The object of the present invention is to provide a novel reaction device and reaction method using fine bubbles with which the problem of fine bubble coalescence is unlikely to occur.

Solution to Problem

The present inventors have discovered that the above problems can be solved by the present invention having the following Aspects.

<<Aspect 1>>

A reaction device for reacting a fine-bubbled gas-phase reactant and a liquid-phase reactant, the device comprising the following:
  a porous body having a plurality of flow paths, in which the flow paths are separated by porous walls, the porous walls have continuous pores, and the porous body has a reaction catalyst on at least a surface thereof,
  a solution supply part for supplying a solution containing the gas-phase reactant and the liquid-phase reactant to the continuous pores of the porous body, and
  a solution discharge part for discharging a solution containing a reaction product, the solution containing the reaction product being obtained by causing the supplied solution to flow through the continuous pores of the porous body.

<<Aspect 2>>

The reaction device according to Aspect 1, wherein the average flow diameter of the porous body as measured with a palm porometer is 3 μm to 100 μm.

<<Aspect 3>>

The reaction device according to Aspect 1, wherein the plurality of flow paths are constituted by a plurality of inlet flow paths and a plurality of outlet flow paths, and substantially the full amount of the solution is introduced to the inlet flow paths, caused to flow through the continuous pores of the porous body, and discharged from the outlet flow paths.

<<Aspect 4>>

The reaction device according to any one of Aspects 1 to 3, wherein the reaction catalyst is present, carried on carrier particles, in a catalyst layer formed on the surface of the porous body.

<<Aspect 5>>

A reaction method comprising the following steps:
  supplying a solution containing a gas-phase reactant and a liquid-phase reactant to the continuous pores of the porous body from the solution supply part of the reaction device according to any one of Aspects 1 to 4, and
  causing the supplied solution to flow through the continuous pores of the porous body to obtain a solution containing a reaction product from the solution discharge part.

<<Aspect 6>>
The reaction method according to Aspect 5, wherein at least a part of the gas-phase reactant is fine-bubbled before the solution flows through the continuous pores of the porous body.

<<Aspect 7>>
The reaction method according to Aspect 5 or 6, wherein the gas-phase reactant is oxygen or hydrogen.

Advantageous Effects of Invention

According to the device and method of the present invention, the gas-phase reactant and the liquid-phase reactant can be reacted with very high reaction efficiency. Further, according to the device and method of the present invention, since a reaction catalyst affixed to a porous body is used, it is not necessary to recover the reaction catalyst and energy input during the reaction can be reduced.

DESCRIPTION OF EMBODIMENTS

<<Reaction Device>>

The reaction device of the present invention is a reaction device for reacting a fine-bubbled gas-phase reactant and a liquid-phase reactant, the device comprising:
- a porous body having a plurality of flow paths, in which the flow paths are separated by porous walls, the porous walls have continuous pores, and the porous body has a reaction catalyst on at least a surface thereof,
- a solution supply part for supplying a solution containing the gas-phase reactant and the liquid-phase reactant to the continuous pores of the porous body, and
- a solution discharge part for discharging a solution containing a reaction product, the solution containing the reaction product being obtained by causing the supplied solution to flow through the continuous pores of the porous body.

Figure 1:
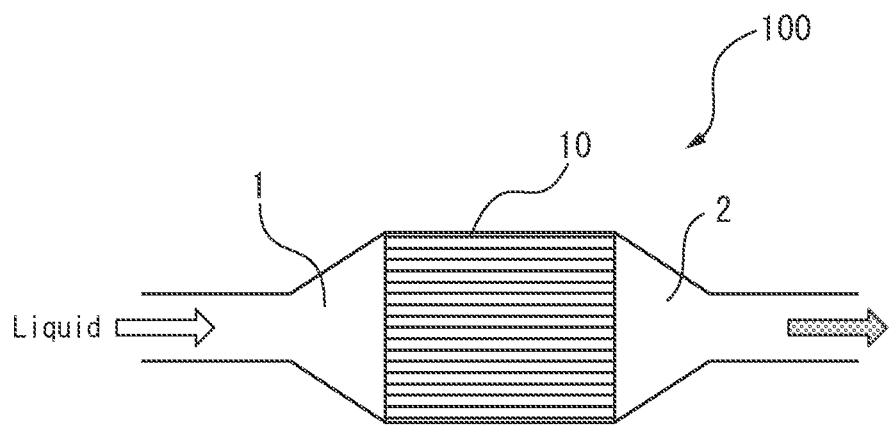
FIG. 1 is a schematic view of an embodiment of the reaction device of the present invention.

In the reaction device of the present invention, for example, as shown in FIG. 1, regarding the reaction device (100) of the present invention, the solution is supplied from the solution supply part (1) to the continuous pores of the porous body (10), the solution flows through the continuous pores of the porous body (10), and a solution containing a reaction product obtained by causing the supplied solution to flow through the continuous pores of the porous body (10) is discharged from the solution discharge part (2).

The present inventors have discovered that when a liquid is flowed through a porous body such as a diesel particulate filter (DPF), fine bubbles are generated in the liquid. It is believed that this is because when a liquid flows through a porous body such as a porous filter substrate, a pressure decrease occurs due to the Venturi effect, whereby gas dissolved in the liquid comes out as fine bubbles. Specifically, when the liquid penetrates into the pores of the porous body from the normal flow path, because the sum of the dynamic pressure and static pressure is maintained due to Bernoulli's theorem, the dynamic pressure becomes very high and the static pressure becomes very low. By reducing the static pressure, the gas dissolved in the liquid comes out as fine bubbles. Since the fine bubbles are unlikely to disappear once formed, it is considered that the fine bubbles remain even if the liquid containing the fine bubbles returns to the normal flow path.

Note that if the pore diameter of the porous body is small to some extent, it is sufficient for the generation of fine bubbles, but if the pore diameter is very small, it is unclear whether a large quantity of fine bubbles is generated accordingly. It is also conceivable that, when the pore diameter has a certain size, the space region in which the fine bubbles are generated becomes wider, and the total number of fine bubbles generated increases.

Further, the present inventors have found that if a reaction catalyst is present in a porous body, when a solution containing a gas-phase reactant to be fine-bubbled and a liquid-phase reactant which is reactive with the gas-phase reactant flows through the porous body, the reaction can proceed with very high reaction efficiency. This is considered to be due to the fact that, immediately after the gas-phase reactant is fine-bubbled by the porous body, the reaction with the liquid-phase reactant is catalyzed by the reaction catalyst present on the surface of the porous body, whereby the reaction can proceed efficiently without coalescence of the fine bubbles.

The solution used in the reaction device of the present invention is not particularly limited as long as it is a solution containing a gas-phase reactant to be fine-bubbled and a liquid-phase reactant which is reactive with the gas-phase reactant. For example, the gas-phase reactant may be dissolved in the solution to be used in advance, using means such as pressurization, or without such means, and may be or may not be fine-bubbled in advance.

The type of the gas-phase reactant is not particularly limited as long as it can be brought into a gaseous state at the temperature and pressure used in the system of the reaction device and can react with the liquid-phase reactant. Examples of the gas-phase reactant include oxygen, hydrogen, nitrogen, argon, carbon dioxide, carbon monoxide, ammonia, methane, ethylene, and acetylene. The gas-phase reactants described in Patent Literature 2 to 4 can also be suitably used.

The type of the liquid-phase reactant is not particularly limited as long as it is in a liquid state or dissolved in a solvent at the temperature and pressure used in the system of the reaction device and can react with the gas-phase reactant. Examples of the liquid-phase reactant include various organic compounds. The liquid-phase reactants described in Patent Literature 2 to 4 can also be suitably used.

The liquid-phase reactant itself may be solid or liquid at the temperature and pressure used in the system of the reaction device. When it is solid, the liquid-phase reactant can be dissolved in a solvent and used. When the solution contains a solvent, examples of the solvent include water-based liquids such as tap water, pure water, and deionized water; aqueous solutions containing a surfactant; and hydrophilic liquids such as methanol and ethanol, and may be an organic solvent.

The gas-phase reactant can be made into fine bubbles having various diameters by changing the pore diameter of the porous body. The average particle diameter of the fine-bubbled gas-phase reactant may be, for example, 100 µm or less, 50 µm or less, 30 µm or less, 10 µm or less, 5 µm or less, 3 µm or less, 1 µm or less, 500 nm or less, 300 nm or less, or 100 nm or less, and may be 10 nm or more, 50 nm or more, 100 nm or more, 300 nm or more, or 500 nm or more. Thus, the fine bubbles obtained in the device of the present invention may be ultrafine bubbles having an average particle diameter of 1 μm or less. The average particle diameter of the ultrafine bubbles can be measured using the NanoSight nanoparticle analysis system (Malvern Panalytical) and the average particle diameter of fine bubbles can be measured using a Microtrac PartAn SI (MicrotracBEL Corporation).

<Porous Body>

The porous body used in the present invention is not particularly limited as long as it is a porous body having a plurality of flow paths, wherein the flow paths are separated by porous walls, has continuous pores, and a reaction catalyst is included on at least a surface thereof. As the solution travels through the flow paths, it contacts the porous walls and flows through the continuous pores of the porous walls, whereby the flow rate of the liquid is locally increased. Specifically, in the liquid in this case, it is believed that the static pressure becomes low as the dynamic pressure increases locally, whereby fine bubbles are generated. The continuous pores may be irregularly shaped.

The material of the porous body is not particularly limited, and may be, for example, a porous metal, a porous ceramic, or a porous resin. Among these, a porous body made of ceramic can be preferably used from the viewpoint of easily obtaining a porous body having preferable continuous pores, and in particular, a porous body having irregularly-shaped continuous pores. Examples of ceramics include, among others, cordierite ($2MgO \cdot 2Al_2O_3 \cdot 5SiO_2$), alumina, silica, zirconia, and silicon carbide.

The pore diameter of the porous body is not particularly limited as long as fine bubbles can be generated thereby, and for example, the average pore diameter as measured with a mercury porosimeter may be 5 μm or more, 8 μm or more, 10 μm or more, or 15 μm or more, and may be 500 μm or less, 300 μm or less, 100 μm or less, 50 μm or less, 30 μm or less, 20 μm or less, or 15 μm or less.

The average flow diameter corresponding to the average pore diameter of the thinnest part of the continuous pores present in the porous body is measured with a palm porometer, and may be 3 μm or more, 5 μm or more, 8 μm or more, 10 μm or more, or 15 μm or more, and may be 500 μm or less, 300 μm or less, 200 μm or less, 100 μm or less, 50 μm or less, 30 μm or less, or 20 μm or less.

The porosity of the porous body is not particularly limited as long as fine bubbles can effectively be generated thereby, and the porosity may be, for example, 30% or more, 40% or more, 50% or more, or 60% or more, and may be 90% or less, 80% or less, 70% or less, or 60% or less. The porosity can be determined from the ratio of the weight of the porous body to the theoretical weight in a medium due to the material of the porous body.

The thickness of the porous body through which the solution flows is not particularly limited as long as fine bubbles can effectively be generated thereby, and the thickness may be, in consideration of fluid pressure loss, 10 mm or less, 5.0 mm or less, 1.0 mm or less, 500 μm or less, 300 μm or less, or 200 μm or less, and may be 100 μm or more, 200 μm or more, or 300 μm or more.

The lengths of the flow paths of the porous body may be 1000 mm or less, 500 mm or less, 400 mm or less, 300 mm or less, 200 mm or less, or 100 mm or less, and may be 30 mm or more, 50 mm or more, 100 mm or more, 200 mm or more, or 300 mm or more.

The porous body may be a so-called straight flow honeycomb substrate in which the flow paths extend substantially in parallel and are adjacent to each other. As such a straight flow honeycomb substrate, a honeycomb substrate well known in the field for producing exhaust gas purification catalysts for automobiles can be used as-is.

Furthermore, among such porous bodies, a porous filter substrate in which a plurality of flow paths are constituted by a plurality of inlet flow paths and a plurality of outlet flow paths, and in which substantially all of the solution flows into the inlet flow paths and flows through the continuous pores in the porous walls, and then flows out of the outlet flow paths is particularly preferable. In this case, a solution can effectively flow through the porous walls at low pressure loss. In particular, the porous filter substrate may be a so-called wall flow honeycomb substrate in which a plurality of inlet flow paths and a plurality of outlet flow paths each extend substantially in parallel and are adjacent to each other.

As such a wall flow honeycomb substrate, a honeycomb substrate well known in the art for producing diesel particulate filters (DPF) or gasoline particulate filters (GPF) can be used as-is.

When the flow paths of the honeycomb substrate are arranged substantially in parallel, the number of flow paths per unit area in a cross-section is referred to as the cell number. The cell number may be, for example, 300 cells/in$^2$ or more, 500 cells/in$^2$ or more, 800 cells/in$^2$ or more, 1000 cells/in$^2$ or more, or 1200 cells/in$^2$ or more, and may be 2000 cells/in$^2$ or less, 1500 cells/in$^2$ or less, 1200 cells/in$^2$ or less, 1000 cells/in$^2$ or less, or 800 cells/in$^2$ or less.

The thickness of the porous walls of the honeycomb substrate may be 1.0 mm or less, 500 μm or less, 300 μm or less, or 200 μm or less, and may be 100 μm or more, 200 μm or more, or 300 μm or more.

Figure 2:
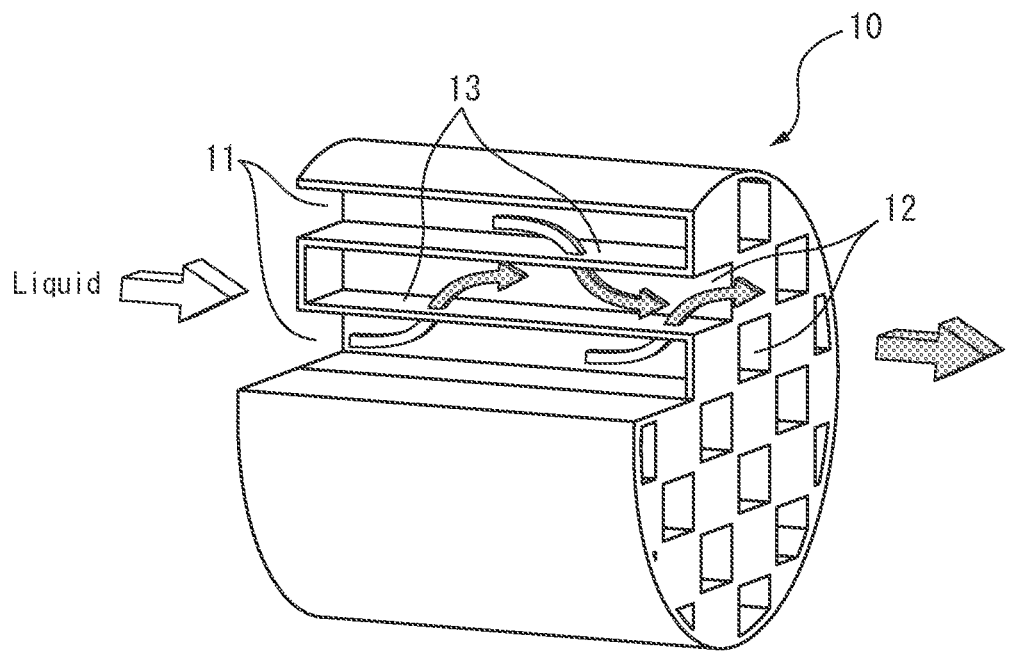
FIG. 2 is a schematic view of an embodiment of a porous body of the device of the present invention.

FIG. 2 is a schematic view of one embodiment of the porous body (10) used in the device of the present invention. The porous body (10) has a plurality of inlet flow paths (11) and a plurality of outlet flow paths (12), the inlet flow paths (11) and the outlet flow paths (12) are separated by porous walls (13), and the plurality of inlet flow paths (11) and the plurality of outlet flow paths (12) extend substantially in parallel to each other and are adjacent to each other. In this porous body (10) (porous filter substrate), a solution flows from the inlet flow paths (11), and fine bubbles are generated when the solution flows through the continuous pores of the porous wall (13). Thereafter, a liquid containing the fine bubbles flows out of the outlet flow paths (12). Note that FIG. 2 is a schematic view, and due to constraints of the drawing, the porous body (10) is illustrated with a very small cell number.

The reaction catalyst present on at least a surface of the porous body is not particularly limited as long as the reaction between the gas-phase reactant and the liquid-phase reactant can be promoted thereby. Furthermore, the reaction catalyst may be affixed only to the porous body, and may be present in a catalyst layer formed on the surface of the porous body carried on the carrier particles. In this case, the reaction catalyst may be a catalyst commonly used in chemical reactions, for example, a metal catalyst, and in particular, a noble metal catalyst such as platinum, palladium, or rhodium, and the carrier particles may be inorganic oxide particles such as silica or alumina.

For example, when a metal reaction catalyst is used, the metal can be affixed to the surface of the porous body by immersing a porous body in an aqueous solution containing a salt of the metal, and thereafter removing the porous body and drying the porous body. In addition, in particular, when a hydrogenation reaction of an organic compound is performed using the reaction device of the present invention, palladium as a reaction catalyst can be affixed to the porous body by immersing the porous body in an aqueous solution containing palladium nitrate and thereafter removing the porous body and drying the porous body.

Furthermore, when the catalyst layer is formed on the surface of the porous body, the catalyst layer may be formed on the surface of the porous body by the so-called wash-coating method, which is known in the field of exhaust gas purification catalysts, and, for example, palladium carried on alumina may be present in the catalyst layer.

<Solution Supply Part and Solution Discharge Part>

The solution supply part used in the device of the present invention is not particularly limited as long as it is capable of supplying a solution to the continuous pores of the porous body. The solution discharge part is not particularly limited as long it can discharge the solution containing the reactants flowing through the continuous pores of the porous body.

Flow paths for circulating the liquid, a container for storing the liquid, a pump for pumping the liquid, a valve for controlling the flow rate of the liquid, and a controller for automated control of the pump and/or the valve may also optionally be present in the solution supply part and the solution discharge part. When at least a part of the gas-phase reactant is fine-bubbled in advance, the solution supply part may comprise a known fine bubble production device, and the solution supply part may further comprise the porous body described above. Furthermore, a person skilled in the art could suitably design the structures thereof in accordance with the application and the place of use of the device.

<<Reaction Method>>

The reaction method of the present invention comprises the following steps:

supplying a solution containing a gas-phase reactant and a liquid-phase reactant to continuous pores of a porous body from a solution supply part of a reaction device as described above, and causing the supplied solution to flow through the continuous pores of the porous body to obtain a solution containing a reaction product from the solution discharge part.

Regarding the features of the reaction method of the present invention, reference can be made to the features described with respect to the reaction device of the present invention.

The present invention will be further specifically described by way of the following Examples, but the present invention is not limited thereto.

EXAMPLES

Experiment A. Styrene Hydrogenation Reaction

Figure 3:
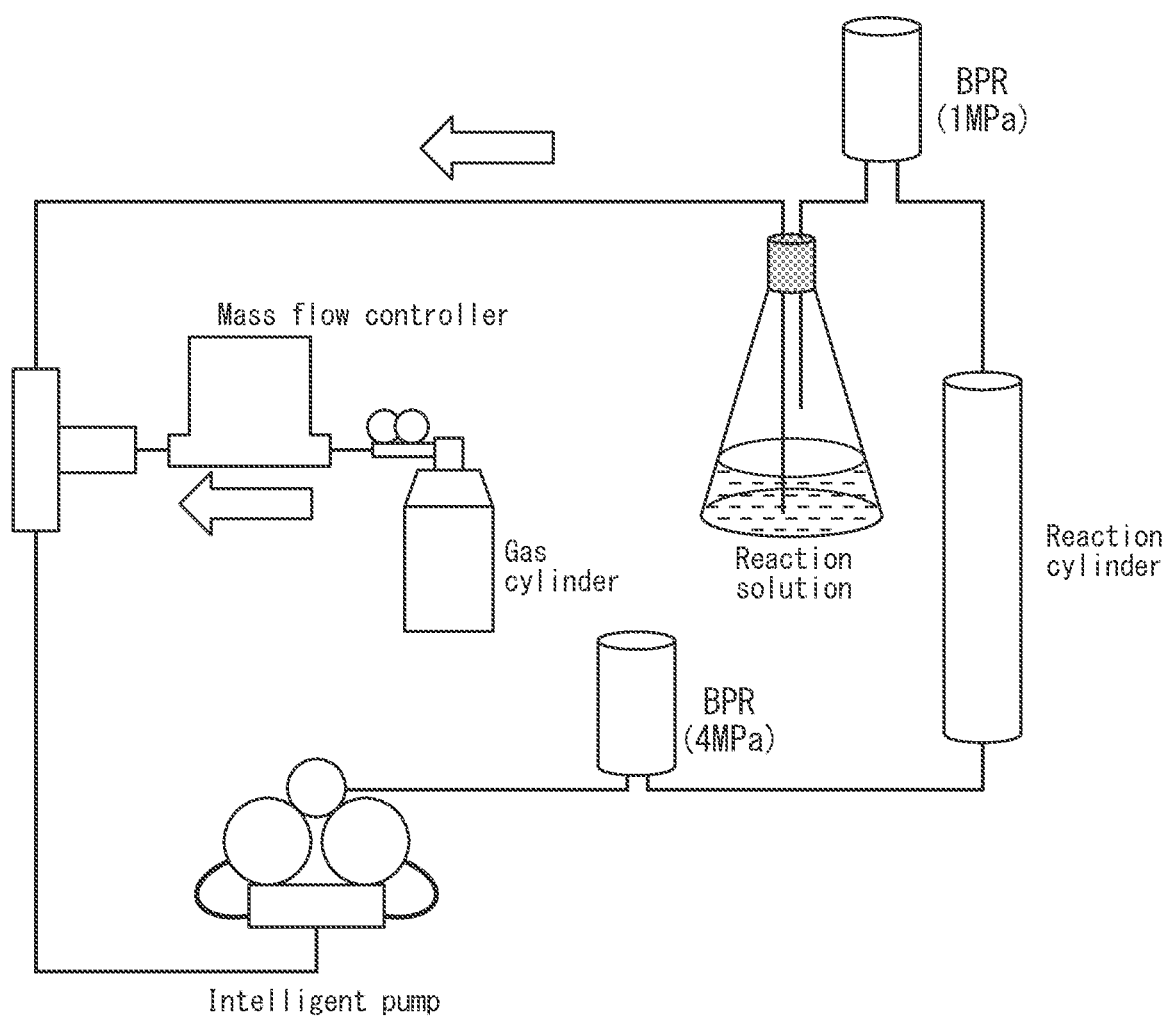
FIG. 3 is schematic view of the reaction device used in the Examples.

A reaction device as illustrated in FIG. 3 was constructed, and using hydrogen as the gas-phase reactant, styrene as the liquid-phase reactant was hydrogenated to obtain ethylbenzene. A methanol solution of styrene was supplied at 5 mL/min, and hydrogen was supplied from a gas cylinder at 2.5 mL/min (substrate equivalent) while being controlled by a mass flow controller. The solution was introduced into the reaction cylinder (25° C., atmospheric pressure) while the pressure was controlled to 4 MPa by back-pressure regulation (BPR).

In Example 1, hydrogen was fine-bubbled in advance immediately after BPR prior to introduction of the solution into the reaction cylinder. Further, as a reaction cylinder, a wall flow honeycomb substrate was used, and the reaction was carried out at room temperature (25° C.). This honeycomb substrate had a catalyst layer on the surface thereof, and this catalyst layer contained palladium carried on alumina particles. In Example 2, the reaction was carried out in the same manner as in Example 1, except that hydrogen was not fine-bubbled in advance.

The cell number of the honeycomb substrate was 300 cells/in$^2$, the thickness of the porous walls was 330 μm, the average pore diameter was 12 μm, the average flow diameter was 8.8 μm, and the porosity was 48%. Note that the average flow diameter was measured with a palm porometer. Specifically, measurement was carried out using a palm porometer manufactured by Porous Materials, Inc., under the condition of WetUP/DryUP (Galwick/air) by the bubble point method at a tortuosity factor of 0.715. Note that, regarding the average pore diameter and porosity, though the numerical values indicated by the distributors of the porous filter substrates were used, these values were measured by the above method.

As Comparative Examples 1 and 2, reactions were carried out in the same manner as in Examples 1 and 2, respectively, except that the palladium carried on alumina particles was introduced into the reaction cylinder in the form of pellets. Each reaction cylinder contained 0.44 mmol of palladium.

The reaction device was operated such that the total amount of the prepared styrene solution was passed through the reaction device once. The conversion rate of the styrene hydrogenation reaction was evaluated. The results are shown in Table 1.

TABLE 1

|  | Ex 1 | Ex 2 | Comp Ex 1 | Comp Ex 2 |
| --- | --- | --- | --- | --- |
| Reaction cylinder | Wall flow | Wall flow | Pellet | Pellet |
| Advance fine-bubbleization | Yes | No | Yes | No |
| Conversion rate [%] | 49.1 | 28.7 | 3.9 | 3.1 |

In Example 1, in which the gas-phase reactant was fine-bubbled in advance (advance fine-bubbleization), the styrene was hydrogenated to ethylbenzene at a conversion as high as 49.1% by simply allowing the styrene to flow through the reaction cylinder once. Furthermore, in Example 2, in which advance fine-bubbleization was not carried out, the styrene was hydrogenated to ethylbenzene at a very high conversion rate.

Experiment B. Toluene Hydrogenation Reaction

Toluene was hydrogenated to obtain methylcyclohexane in the same manner as in Experiment A above.

In Example 3, prior to introduction of the solution into the reaction cylinder, the hydrogen was fine-bubbled in advance. Furthermore, the reaction was carried out using a straight flow honeycomb substrate as the reaction cylinder at 80° C. and 1 MPa. This honeycomb substrate had a catalyst layer on the surface thereof, and this catalyst layer contained rhodium carried on alumina particles. In Example 4, the reaction was carried out in the same manner as in Example 3, except that the hydrogen was not fine-bubbled in advance.

The cell number of the honeycomb substrate was 400 cells/in$^r$, the thickness of the porous walls was 170 μm, the average pore diameter was 5.0 μm, the average flow diameter was 4.0 μm, and the porosity was 28%.

As Comparative Examples 3 and 4, reactions were carried out in the same manner as in Examples 3 and 4, respectively, except that the rhodium carried on alumina particles was introduced into the reaction cylinder in the form of pellets. Each reaction cylinder contained 0.46 mmol of rhodium.

The reaction device was operated for 150 minutes to evaluate the reaction rate of toluene with hydrogen. The evaluation results are shown in Table 2.

TABLE 2

|  | Ex 3 | Ex 4 | Comp Ex 3 | Comp Ex 4 |
| --- | --- | --- | --- | --- |
| Reaction cylinder | Straight flow | Straight flow | Pellet | Pellet |
| Advance fine-bubbleization | Yes | No | Yes | No |
| Reaction rate [μmol/min] | 7.11 | 6.36 | 0.21 | 0.30 |

In this reaction system, in which the catalyst was in pellet form, the reaction rate was very slow, whereas when a honeycomb substrate was used, toluene could be hydrogenated at a very high reaction rate.

REFERENCE SIGNS LIST 1 solution supply part
2 solution discharge part
10 porous body
11 inlet flow path
12 outlet flow path
13 porous wall
100 device

The invention claimed is:

1. A reaction method comprising the following steps:
supplying a solution containing a gas-phase reactant and a liquid-phase reactant to a reaction device for reacting a fine-bubbled gas-phase reactant and a liquid-phase reactant so that the supplied solution is supplied to continuous pores of a porous body from a solution supply part, the reaction device comprising:
the porous body having a plurality of flow paths, in which the flow paths are separated by porous walls, the porous walls having the continuous pores, and the porous body having a reaction catalyst on at least a surface thereof,
the solution supply part configured to supply the solution containing the gas-phase reactant and the liquid-phase reactant to the continuous pores of the porous body, and
a solution discharge part configured to discharge a solution containing a reaction product, the solution containing the reaction product being obtained by causing the supplied solution to flow through the continuous pores of the porous body, and
causing the supplied solution to flow through the continuous pores of the porous body to obtain the solution containing a reaction product from the solution discharge part,
wherein an average particle diameter of the fine-bubbled gas-phase reactant is 1 μm or less.

2. The reaction method according to claim 1, wherein at least a part of the gas-phase reactant is fine-bubbled before the solution flows through the continuous pores of the porous body.

3. The reaction method according to claim 1, wherein the gas-phase reactant is oxygen or hydrogen.

4. The reaction method according to claim 2, wherein the gas-phase reactant is oxygen or hydrogen.

5. The reaction method according to claim 1, wherein the average flow diameter of the porous body as measured with a palm porometer is 3 μm to 100 μm.

6. The reaction method according to claim 1, wherein the plurality of flow paths are constituted by a plurality of inlet flow paths and a plurality of outlet flow paths, and
substantially the full amount of the solution is introduced to the inlet flow paths, caused to flow through the continuous pores of the porous body, and discharged from the outlet flow paths.

7. The reaction method according to claim 1, wherein the reaction catalyst is present, carried on carrier particles, in a catalyst layer formed on the surface of the porous body.

8. The reaction method according to claim 5, wherein the reaction catalyst is present, carried on carrier particles, in a catalyst layer formed on the surface of the porous body.

9. The reaction method according to claim 6, wherein the reaction catalyst is present, carried on carrier particles, in a catalyst layer formed on the surface of the porous body.

10. The reaction method according to claim 1, wherein
the gas-phase reactant is dissolved in the solution containing the gas-phase reactant and the liquid-phase reactant, and
the gas-phase reactant dissolved in the solution containing the gas-phase reactant and the liquid-phase reactant comes out as ultra-fine bubbles when the solution flows through the continuous pores of the porous body.

* * * * *